US012564564B2

(12) United States Patent
Ding

(10) Patent No.: US 12,564,564 B2
(45) Date of Patent: Mar. 3, 2026

(54) COMPOSITION COMPRISING TYROSOL AND AMINO ACIDS AND ITS APPLICATION IN ENHANCING ATHLETIC PERFORMANCE AND COMBATING FATIGUE

(71) Applicant: MolTek Nutrition Co., Ltd, Nanjing (CN)

(72) Inventor: Feng Ding, Nanjing (CN)

(73) Assignee: MolTek Nutrition Co., Ltd, Nanjing (CN)

( * ) Notice: Subject to any disclaimer, the term of this patent is extended or adjusted under 35 U.S.C. 154(b) by 0 days.

(21) Appl. No.: 18/957,761

(22) Filed: Nov. 24, 2024

(65) Prior Publication Data

US 2026/0021065 A1 Jan. 22, 2026

(30) Foreign Application Priority Data

Jul. 22, 2024 (CN) ......................... 202410979761.X
Oct. 21, 2024 (CN) .......................... 202411471319.2

(51) Int. Cl.
*A61K 31/198* (2006.01)
*A61K 31/05* (2006.01)
*A61P 21/00* (2006.01)

(52) U.S. Cl.
CPC ............ *A61K 31/198* (2013.01); *A61K 31/05* (2013.01); *A61P 21/00* (2018.01)

(58) Field of Classification Search
CPC ........ A61K 31/198; A61K 31/05; A61P 21/00
See application file for complete search history.

(56) References Cited

FOREIGN PATENT DOCUMENTS

| CN | 109295113 A | 2/2019 | |
| CN | 116064704 A | 5/2023 | |
| CN | 116964211 A | 10/2023 | |
| WO | WO-2017040421 A1 * | 3/2017 | ........... A61K 31/198 |

OTHER PUBLICATIONS

Markhali (Processes, 2020, 8, 1177) (Year: 2020).*
Luciano, J. Cardiovasc Pharmacol, vol. 57, No. 6, Jun. 2011 (Year: 2011).*
Malec, J. Chromatogr. A 1523, 2017, 248-256 (Year: 2017).*

* cited by examiner

*Primary Examiner* — Susanna Moore
*Assistant Examiner* — Luisalberto Gonzalez
(74) *Attorney, Agent, or Firm* — Nitin Kaushik

(57) ABSTRACT

The present invention discloses a composition containing tyrosol and amino acids, and its application in enhancing athletic performance and anti-fatigue. The amino acids are citrulline and/or arginine. The supplementation of tyrosol in combination with citrulline and/or arginine can increase the rate of nitric oxide production and extend the duration of nitric oxide activity, promoting vasodilation and blood flow. This, in turn, enhances athletic performance, improves endurance, and combats fatigue.

3 Claims, 6 Drawing Sheets

COMPOSITION COMPRISING TYROSOL AND AMINO ACIDS AND ITS APPLICATION IN ENHANCING ATHLETIC PERFORMANCE AND COMBATING FATIGUE

CROSS-REFERENCE TO RELATED APPLICATIONS

The application claims priority to Chinese patent application No. 202410979761X, filed on Jul. 22, 2024, and Chinese patent application No. 2024114713192, filed on Oct. 21, 2024, the entire contents of which are incorporated herein by reference.

TECHNICAL FIELD

The present invention relates to a composition comprising tyrosol and amino acids, particularly to a composition comprising tyrosol and amino acids and a nitric oxide booster, and its application in enhancing athletic performance and combating fatigue.

BACKGROUND

Nitric oxide (NO) is an important signaling molecule that regulates blood flow and prevents blood components from adhering to the vessel walls, playing a crucial physiological role in maintaining cardiovascular health. Research has shown that a deficiency of nitric oxide is a common feature of several cardiovascular diseases, including diabetes, atherosclerosis, and hypertension. Additionally, sports physiology studies have confirmed NO's significant role in controlling vasodilation, blood flow rates, and mitochondrial respiration, thereby enhancing athletic performance. Therefore, it can be considered that athletic performance is positively correlated with NO levels. Many athletes, fitness enthusiasts, and "weekend warriors" (those who engage in intense physical activities only on weekends, especially indoor workers) seek to achieve excellent athletic performance by continuously improving their exercise methods and seeking various supplements to increase endurance, strength, and more. Many sports nutrition supplements at home and abroad claim to enhance athletic performance, one of their main functions being to promote NO production. This allows athletes to experience sustained increases in NO levels during exercise, enhancing vasodilation, which can promote the delivery of oxygen and nutrients to muscle tissues and timely removal of metabolic waste products. The result is a better exercise experience, noticeable "pump" feeling, prolonged endurance, and less fatigue.

The NO responsible for the aforementioned "pump" feeling is primarily produced in vascular endothelial cells, where endothelial nitric oxide synthase (eNOS) catalyzes the substrate L-arginine to produce NO and L-citrulline. L-citrulline can also be converted to L-arginine in the body, and supplementing L-citrulline can enhance NO production more effectively than L-arginine, this is because L-arginine is readily absorbed and metabolized by various types of cells into other substances, affecting NO production, whereas L-citrulline does not involve multiple metabolic pathways. Nowadays, L-citrulline and L-arginine are widely used as NO "boosters" in sports supplements. Clinical researches have confirmed that supplementation with L-citrulline or L-arginine can enhance athletes' endurance and muscle strength, thereby improving athletic performance. Research reports indicate that the primary mechanism by which L-arginine supplements enhance muscle strength and energy production is as a substrate for endogenous NO synthesis. This is because NO-mediated increased blood flow enhances skeletal muscle performance, hypertrophy, and strength adaptation. However, due to the very short half-life of NO, ranging from a few milliseconds to a few seconds, continuous production is essential for its function.

Therefore, there is an urgent need to address the technical issue of sustaining nitric oxide (NO) to enhance athletic performance and combat fatigue.

SUMMARY

The purpose of the present invention is to address the shortcomings of the prior art and provide a composition comprising: (a) tyrosol and/or tyrosol derivatives, and (b) amino acids and/or amino acid derivatives; wherein the amino acids are citrulline and/or arginine.

Specifically, the amino acids and/or amino acid derivatives are citrulline and its derivatives, salts, esters, and arginine and its derivatives, salts, esters, such as citrulline malate and arginine silicate.

Tyrosol and/or tyrosol derivatives include salts, esters, acids, ketones, polymers, co-crystals, chelates, complexes, glycosides, hydrates, and substances formed by non-chemical bonding with other substances. Tyrosol derivatives are digested or metabolized in the body to form tyrosol or exhibit the same or similar physiological effects as tyrosol.

Citrulline and/or citrulline derivatives, wherein the derivatives include salts, esters, acids, ketones, polymers, co-crystals, chelates, complexes, glycosides, hydrates, and substances formed by non-chemical bonding with other substances. Citrulline derivatives are digested or metabolized in the body to form citrulline or exhibit the same or similar physiological effects as citrulline.

Arginine and/or arginine derivatives, wherein the derivatives include salts, esters, acids, ketones, polymers, co-crystals, chelates, complexes, glycosides, hydrates, and substances formed by non-chemical bonding with other substances. Arginine derivatives are digested or metabolized in the body to form arginine or exhibit the same or similar physiological effects as arginine.

Further, the composition comprises (a) tyrosol and/or tyrosol derivatives and (b) amino acids and/or amino acid derivatives in a ratio of (0.02-0.5):(1-0.1). Furthermore, the composition comprises (a) tyrosol and/or tyrosol derivatives and (b) amino acids and/or amino acid derivatives in a ratio of (0.02-0.5):(0.8-0.1), (0.02-0.5):(0.6-0.1), (0.02-0.5):(1-0.5), (0.02-0.5):(0.8-0.5), (0.02-0.5):(0.6-0.5).

The product of the composition described in the present invention can be formulated in various forms, including but not limited to common pharmaceutical forms such as powders, suppositories, gels, oral liquids, hard capsules, soft capsules, as well as common forms for health foods and dietary supplements such as beverages, solid beverages, soft drinks, hard capsules, soft capsules, multilayer hard capsules, dissolvable tablets, lyophilized powders, milk tablets, chocolate, filled gummies, filled chocolates, tea beverages, and cold brew coffee.

The present invention also provides for the use of a composition for rapidly increasing NO levels, comprising: (a) tyrosol and/or tyrosol derivatives, and (b) amino acids and/or amino acid derivatives; wherein the amino acids are citrulline and/or arginine.

The present invention also provides for the use of a composition for extending the duration of NO activity, comprising: (a) tyrosol and/or tyrosol derivatives, and (b)

amino acids and/or amino acid derivatives; wherein the amino acids are citrulline and/or arginine.

The present invention also provides for the use of a composition for enhancing athletic performance, and/or increasing endurance, and/or combating fatigue, and/or enhancing muscle pump, comprising: (a) tyrosol and/or tyrosol derivatives, and (b) amino acids and/or amino acid derivatives; wherein the amino acids are citrulline and/or arginine.

Furthermore, enhancing athletic performance, and/or increasing endurance, and/or combating fatigue, includes faster muscle activation, rapid increase in muscle strength, extending time to exhaustion, improving VO2 max, increasing muscle strength, and reducing fatigue-related biochemical markers.

The present invention also provides a sports supplement, the sports supplement comprising a composition, including (a) tyrosol and/or tyrosol derivatives, and (b) amino acids and/or amino acid derivatives; wherein the amino acids are citrulline and/or arginine.

Furthermore, the sports supplement includes proteins, polypeptides, amino acids, carbohydrates, vitamins, and minerals.

Beneficial Effects: The supplementation of tyrosol in combination with citrulline and/or arginine can increase the rate of NO production and extend the duration of NO activity, promoting vasodilation and blood flow. Consequently, this enhances athletic performance, improves endurance, and combats fatigue.

DETAILED DESCRIPTION OF THE EMBODIMENTS

Example 1

Figure 1:
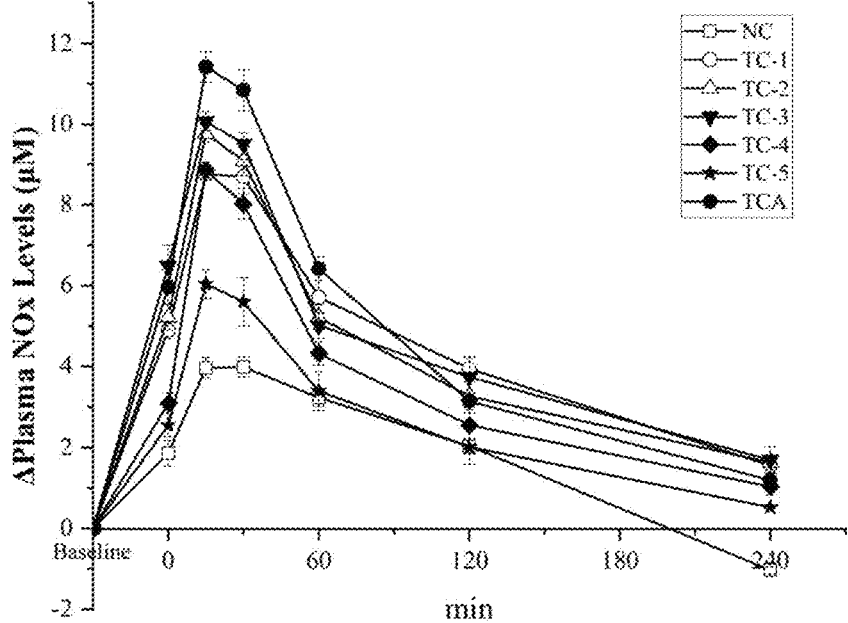
FIG. 1: Change in NOx levels after administration of compositions with varying ratios of tyrosol and L-citrulline.

A composition comprising tyrosol and an amino acid; wherein the amino acid is citrulline. The ratio of tyrosol to the amino acid is 0.02:1.

Example 2

A composition comprising tyrosol and an amino acid; wherein the amino acid is citrulline. The ratio of tyrosol to the amino acid is 0.04:1.

Example 3

A composition comprising tyrosol and an amino acid; wherein the amino acid is citrulline. The ratio of tyrosol to the amino acid is 0.1:1.

Example 4

A composition comprising tyrosol and an amino acid; wherein the amino acid is citrulline. The ratio of tyrosol to the amino acid is 0.5:0.5.

Example 5

A composition comprising tyrosol and an amino acid; wherein the amino acid is citrulline. The ratio of tyrosol to the amino acid is 0.5:0.1.

Example 6

A composition comprising tyrosol and an amino acid; wherein the amino acid is arginine. The ratio of tyrosol to the amino acid is 0.02:1.

Example 7

A composition comprising tyrosol and an amino acid; wherein the amino acid is arginine. The ratio of tyrosol to the amino acid is 0.04:1.

Example 8

A composition comprising tyrosol and an amino acid; wherein the amino acid is arginine. The ratio of tyrosol to the amino acid is 0.1:1.

Example 9

A composition comprising tyrosol and an amino acid; wherein the amino acid is arginine. The ratio of tyrosol to the amino acid is 0.5:0.5.

Example 10

A composition comprising tyrosol and an amino acid; wherein the amino acid is arginine. The ratio of tyrosol to the amino acid is 0.5:0.1.

Example 11

A composition comprising tyrosol and amino acids; wherein the amino acids are citrulline and arginine. The ratio of tyrosol to the two amino acids is 0.1:1:1.

Experiment 1

Short-term supplementation with a composition of tyrosol and L-citrulline and/or L-arginine enhances nitric oxide production efficiency and duration of action.

Eight-week-old Sprague-Dawley rats were acclimatized for one week in an environment with a temperature of 22±2° C. and a humidity of 55±5%, with free access to water and normal feed. The rats were anesthetized, and a catheter was inserted into the carotid artery to facilitate subsequent blood sampling. After a three-day recovery period, the post-surgical rats were randomly divided into the following groups:

TABLE 1

| | Amounts added by different groups | | |
|---|---|---|---|
| Group | Tyrosol %[a] | L-citrulline %[a] | L-arginine %[a] |
| NC | 0 | 0 | 0 |
| TC-1 | 0.02 | 1 | 0 |
| TC-2 | 0.04 | 1 | 0 |
| TC-3 | 0.1 | 1 | 0 |
| TC-4 | 0.5 | 0.5 | 0 |
| TC-5 | 0.5 | 0.1 | 0 |
| TA-1 | 0.02 | 0 | 1 |
| TA-2 | 0.04 | 0 | 1 |
| TA-3 | 0.1 | 0 | 1 |
| TA-4 | 0.5 | 0 | 0.5 |
| TA-5 | 0.5 | 0 | 0.1 |
| T-1 | 0.5 | 0 | 0 |
| T-2 | 0.02 | 0 | 0 |
| C-1 | 0 | 1 | 0 |
| C-2 | 0 | 0.1 | 0 |
| A-1 | 0 | 0 | 1 |
| A-2 | 0 | 0 | 0.1 |
| TCA | 0.1 | 1 | 1 |

Note: "a" denotes the addition amount as the dry weight percentage (w/w %) of feed added to the diet.

After three days of feeding, blood samples were collected from each group of rats at 0, 15, 30, 60, 120, and 240 minutes after the end of feeding on the third day to measure the levels of nitric oxide metabolites nitrite and nitrate (NOx) using a colorimetric method. Based on the equal molar concentration relationship between nitrite, nitrate, and nitric oxide (NO), thereby indirectly measuring the nitric oxide (NO) concentration in serum, that is, NO levels can be represented by NOx levels.

Figure 2:
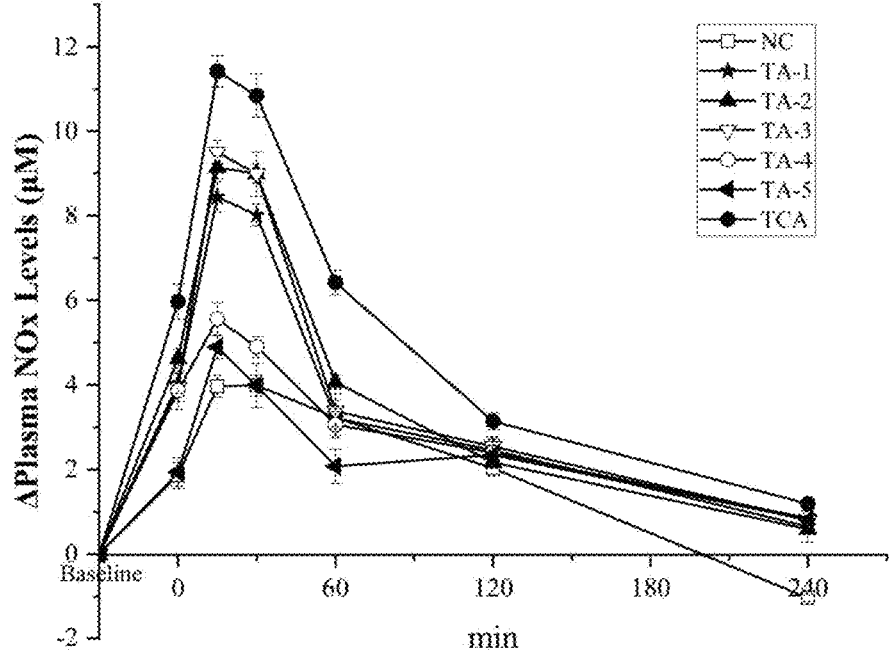
FIG. 2: Change in NOx levels after administration of compositions with varying ratios of tyrosol and L-arginine.

As shown in FIGS. 1 and 2, the NOx levels in rats supplemented with a composition of tyrosol and L-citrulline and/or L-arginine reached their peak more rapidly (peaking at 15 minutes) and the peak values were generally higher compared to the supplementation of tyrosol or L-citrulline or L-arginine alone (peaking at 30 minutes). This indicates that the combination of tyrosol and NO-producing amino acids can enhance the efficiency of NO production. The peak levels and overall curve trends of the composition containing tyrosol, L-citrulline, and L-arginine (TCA) were higher than those of other groups.

Tyrosol, a natural phenylethanoid, is derived from phenylethanol. This colorless solid compound helps protect cells from oxidative damage. In the human diet, the primary source of tyrosol is olive oil. The benefits of consuming olive oil are well-known, including lowering blood lipids, reducing thrombus formation, and helping to reduce the risk of cardiovascular diseases. Researchers have studied numerous active components in olive oil, and in exploring the potential of tyrosol in cardiovascular disease, it was found that tyrosol can enhance eNOS activity, indirectly promoting NO production. Since eNOS is the key enzyme catalyzing NO production, increasing its activity may help boost NO production efficiency. It has been reported that tyrosol can promote NO production.

Figure 3:
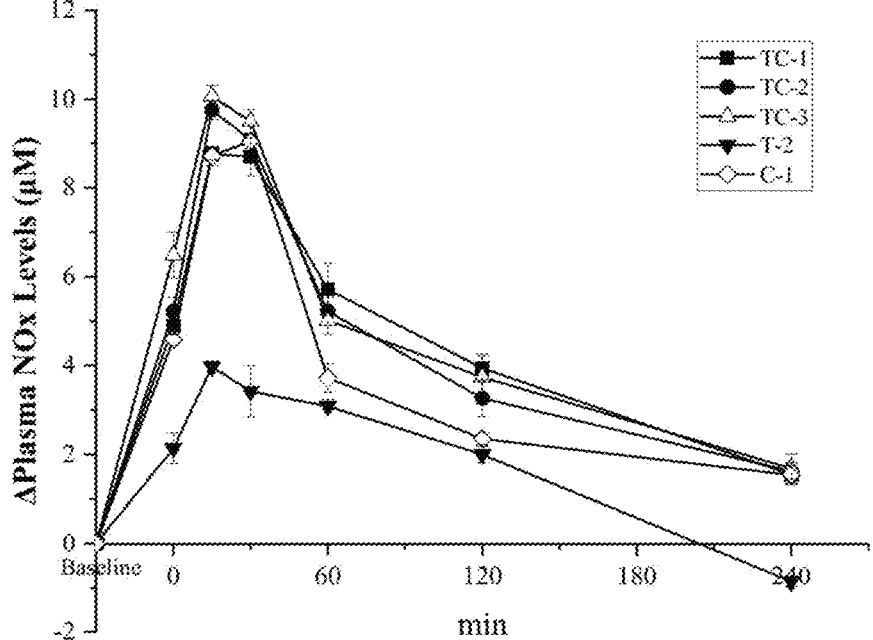
FIG. 3: Comparison of change in NOx levels after administration of compositions with varying ratios of tyrosol and L-citrulline versus tyrosol or citrulline alone.
Figure 5:
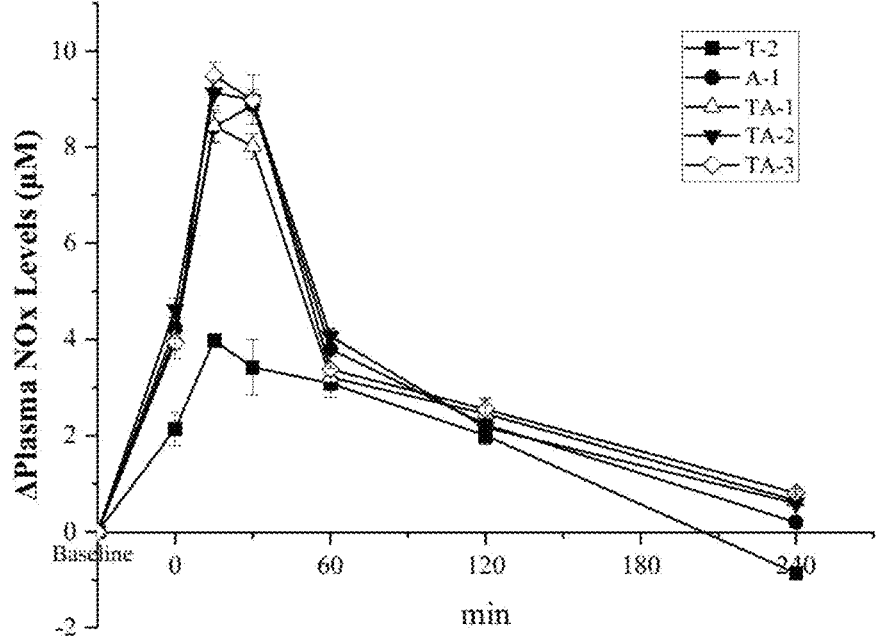
FIG. 5: Comparison of change in NOx levels after administration of compositions with varying ratios of tyrosol and L-arginine versus tyrosol or arginine alone.

However, the inventors have found that supplementation with a composition of tyrosol and citrulline and/or arginine can enhance NO production efficiency. As shown in FIGS. 3 and 5, supplementation with a low amount (0.02%) of tyrosol alone (T-2) does not significantly increase NO production, but in combination with a higher amount (1%) of L-citrulline or L-arginine (TC-1, TA-1), the NO production peak is reached at 15 minutes. With the same amount (1%) of amino acids, higher amounts (0.04%, 0.1%) of tyrosol (TC-2, TC-3, TA-2, TA-3) result in both higher peak levels and overall curve trends compared to other groups, indicating that higher amounts of tyrosol can significantly enhance the NO production capacity and efficiency of the two amino acids.

Figure 4:
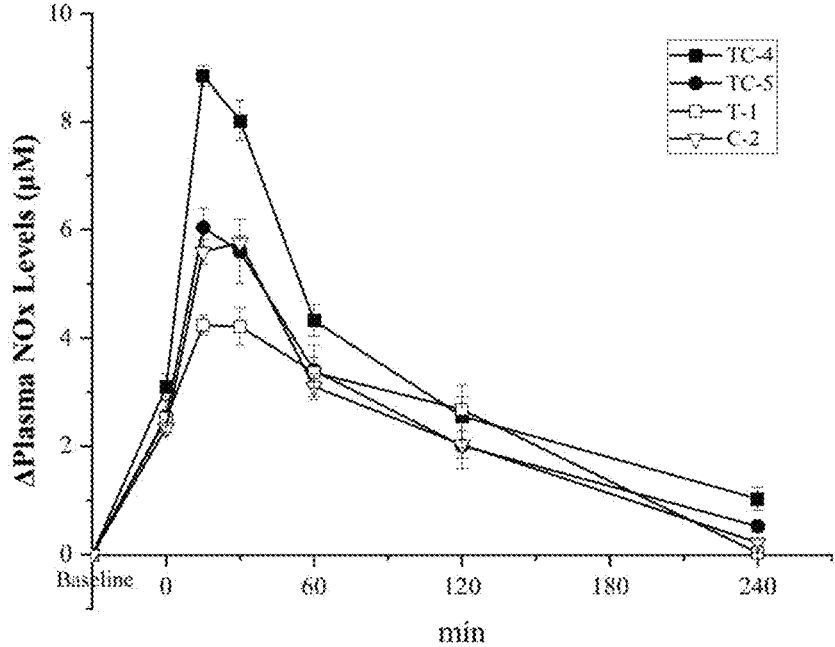
FIG. 4: Comparison of change in NOx levels after administration of compositions with varying ratios of tyrosol and L-citrulline versus tyrosol or citrulline alone.
Figure 6:
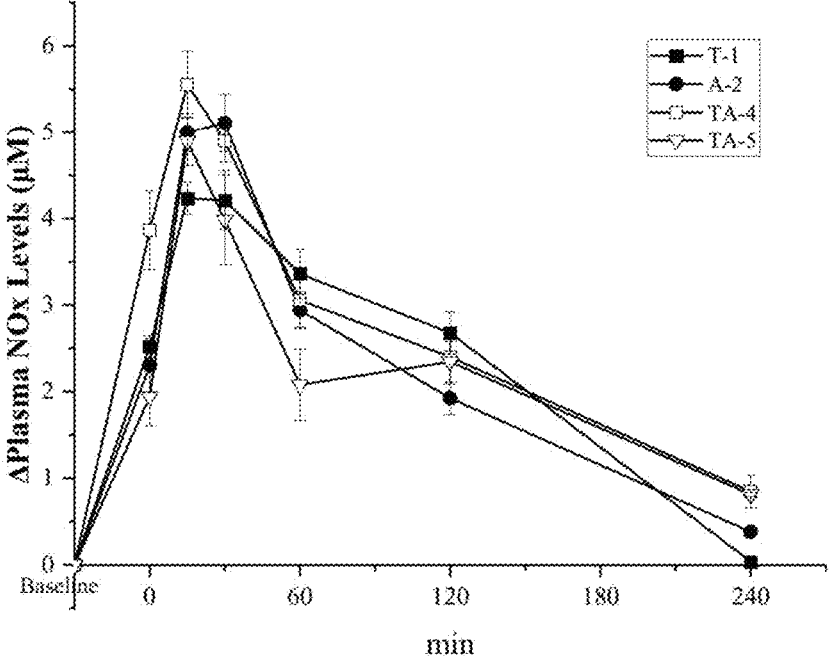
FIG. 6: Comparison of change in NOx levels after administration of compositions with varying ratios of tyrosol and L-arginine versus tyrosol or arginine alone.

The compositions with other ratios compared to the single amino acid groups with the same addition amount follow the same pattern. As shown in FIGS. 4 and 6, the peak time of NO production in rats supplemented with tyrosol and amino acid compositions advanced to 15-minute timepoint. The groups with higher addition amounts (0.5%) of the two amino acids and tyrosol (TC-4, TA-4) produced higher NO peak levels than the groups with lower addition amounts (0.1%) of amino acids, however, when the supplementation with 0.5% tyrosol (TC-5, TA-5) also advanced the peak time, indicating improved NO production efficiency.

TABLE 2

| | Peak variation and times to reach peak NOx level ($\mu M$) for each group | | |
|---|---|---|---|
| Group | 15 min | 30 min | 240 min |
| NC | 3.97 | 3.99 | −1.03 |
| TC-1 | 8.75 | 8.70 | 1.55 |
| TC-2 | 9.76 | 9.08 | 1.63 |
| TC-3 | 10.07 | 9.50 | 1.69 |
| TC-4 | 8.86 | 8.02 | 1.03 |
| TC-5 | 6.04 | 5.6 | 0.52 |
| T-1 | 4.23 | 4.21 | 0.03 |
| T-2 | 3.98 | 3.42 | −0.86 |
| C-1 | 8.72 | 9.04 | 1.54 |
| C-2 | 5.59 | 5.76 | 0.22 |
| A-1 | 8.41 | 8.89 | 0.20 |
| A-2 | 5.00 | 5.11 | 0.38 |
| TA-1 | 8.44 | 8.01 | 0.65 |
| TA-2 | 9.13 | 8.99 | 0.59 |
| TA-3 | 9.50 | 8.99 | 0.81 |
| TA-4 | 5.55 | 4.90 | 0.85 |
| TA-5 | 4.90 | 3.99 | 0.81 |
| TCA | 11.42 | 10.85 | 1.19 |

From Table 2, it can be clearly seen that the NOx levels in the supplemented compositions (tyrosol with L-citrulline, tyrosol with L-arginine, tyrosol with both amino acids) at 15 minutes are higher than at 30 minutes, indicating an earlier peak and increased NO production efficiency. At 240 minutes post-supplementation, the change in NOx levels in the normal control group is negative, indicating that NO levels are slightly below baseline after 4 hours. In contrast, in other supplemented experimental groups, except for the low-dose tyrosol group (0.02% T-2), NO levels at 240 minutes remain above baseline. Additionally, at 240 minutes, the NOx levels in the compositions are generally higher than those in the corresponding single tyrosol or single amino acid groups with same doses. The combination of tyrosol, L-citrulline, and L-arginine (TCA) shows the highest NO levels at 240 minutes. This indicates that the supplemented compositions not only advance the time to peak NO levels but also slow the NO metabolism rate, maintain NO levels, and extend the duration of NO activity.

Experiment 2

Long-term supplementation with a composition of tyrosol and L-citrulline and/or L-arginine improves athletic performance: faster muscle activation, rapid increase in muscle strength, enhanced endurance in mice, and reduced fatigue biochemical markers.

Six-week-old male C57BL/6J mice were acclimatized for one week in an environment with a temperature of 22±2° C. and a humidity of 55±5%, with free access to water and normal feed. They were then randomly divided into the following groups:

Normal resting mice (ND),

Exercise mice (ED),

Composition 1 (Cmix, diet supplemented with 0.1% w/w tyrosol, 1% w/w L-citrulline), Composition 2 (Amix, diet supplemented with 0.1% w/w tyrosol, 1% w/w L-arginine), Composition 3 (Allmix, diet supplemented with 0.1% w/w tyrosol, 1% w/w L-citrulline, 1% w/w L-arginine), Tyrosol (TYR, diet supplemented with 0.1% w/w tyrosol), L-citrulline (CIT, diet supplemented with 1% w/w L-citrulline), L-arginine (ARG, diet supplemented with 1% w/w L-arginine).

After continuous feeding for 14 days, the mice were placed on a metabolic treadmill to perform a maximum oxygen consumption test (VO2 max). Following the test, the mice were fed for an additional two weeks. Grip strength of the mice was measured using a grip strength meter at 15 and 30 minutes after the last feeding. Three days later, a 5% body weight tin wire and detector were attached to the tail of the mice, and they were placed in a loaded swimming tank with water at $30 \pm 1°$ C. for an exhaustion swimming test. Exhaustion was defined as the mice touching the bottom continuously three times within 30 seconds. Upon detection of exhaustion, the swimming tank automatically lifted the mice, and the exhaustion swimming time was recorded. After the test, blood was collected, serum was separated, and lactic acid levels were measured using a biochemical analyzer.

TABLE 3

| VO2 max results | |
| --- | --- |
| Group | VO2 max (ml/kg/min) |
| ED | 42 |
| Cmix | 62 |
| Amix | 54 |
| Allmix | 60 |
| TYR | 44 |
| CIT | 51 |
| ARG | 52 |

As shown in Table 3, supplementation with a composition of tyrosol and L-citrulline or L-arginine can increase VO2 max levels, which are higher than those achieved with tyrosol, L-citrulline, or L-arginine alone. This indicates that the supplemented composition can further enhance aerobic exercise performance.

TABLE 4

| Grip strength results | | | |
| --- | --- | --- | --- |
| | Grip strength (gf) | | Change in grip |
| Group | 15 min | 30 min | strength (gf) |
| ED | 198.4 | 181.3 | −17.1 |
| Cmix | 263.7 | 254.4 | −9.3 |
| Amix | 242.4 | 228.1 | −14.3 |
| Allmix | 274.3 | 265.6 | −8.7 |
| TYR | 232.5 | 215.7 | −16.8 |
| CIT | 260.4 | 248.8 | −11.6 |
| ARG | 222.1 | 198.2 | −23.9 |

As shown in Table 4, the grip strength of mice supplemented with a composition of tyrosol and L-citrulline or L-arginine is higher at 15 minutes post-supplementation compared to mice supplemented with tyrosol, or L-citrulline, or L-arginine alone. At 30 minutes, the grip strength of mice in the composition groups remains similar to the levels at 15 minutes, while the grip strength in the groups supplemented with each nutrient alone decreases more significantly and are lower than the corresponding composition groups. This indicates that the composition of tyrosol and L-citrulline or L-arginine can more quickly activate muscle performance, rapidly increase muscle strength, and maintain it at a higher level.

TABLE 5

| Exhausted swimming time | |
| --- | --- |
| Group | Time (s) |
| ED | 240.5 |
| Cmix | 626.5 |
| Amix | 588.3 |
| Allmix | 652.1 |
| TYR | 357.6 |
| CIT | 601.4 |
| ARG | 566.3 |

As shown in Table 5, supplementation with a composition of tyrosol and L-citrulline or L-arginine extends the time to exhaustion in mice compared to supplementation with tyrosol, L-citrulline, or L-arginine alone, thereby further enhancing the endurance of the mice.

TABLE 6

| Lactic acid level in plasma | |
| --- | --- |
| Group | Lactic acid (mmol/L) |
| ND | 2.54 |
| ED | 4.86 |
| Cmix | 3.74 |
| Amix | 3.62 |
| Allmix | 3.72 |
| TYR | 4.45 |
| CIT | 4.11 |
| ARG | 4.22 |

As shown in Table 6, supplementation with a composition of tyrosol and L-citrulline or L-arginine significantly reduces post-exercise lactate levels in mice compared to supplementation with tyrosol, L-citrulline, or L-arginine alone. This indicates that the composition of tyrosol and L-citrulline or L-arginine provides superior anti-fatigue effects.

It will be understood by those skilled in the art that, unless otherwise defined, all terms (including technical and scientific terms) used herein have the same meaning as commonly understood by one of ordinary skill in the art to which this invention belongs. It should also be understood that terms, such as those defined in general dictionaries, should be interpreted as having a meaning consistent with the context of the relevant art, and unless otherwise defined, should not be interpreted in an idealized or overly formal sense.

It should be understood that the detailed description of the invention provided through preferred embodiments is illustrative and not restrictive. Those skilled in the art may make modifications to the technical solutions described in the embodiments or make equivalent substitutions for some of the technical features without departing from the spirit and scope of the technical solutions of the present invention.

What is claimed is:

1. A method for extending the duration of NO activity in a human subject, comprising administering a composition consisting of:

(a) tyrosol, and (b) amino acids and/or amino acid derivatives; wherein the amino acids are citrulline and/or arginine; wherein amino acid derivatives are amino acid salts and/or amino acid esters;

wherein the ratio of (a) tyrosol to (b) amino acids and/or amino acid derivatives is (0.02-0.5):(1-0.5).

2. The method of claim 1, wherein the composition is for enhancing athletic performance, and/or increasing endurance, and/or combating fatigue, and/or enhancing muscle pump.

3. The method of claim 2, wherein the enhancing athletic performance, and/or increasing endurance, and/or combating fatigue, and/or enhancing muscle pump comprises: faster muscle activation, rapid muscle strength increase, extending time to exhaustion, improving VO2 max, increasing muscle strength, and reducing fatigue-related biochemical markers.

\* \* \* \* \*